United States Patent
Paulson

(10) Patent No.: US 10,136,693 B1
(45) Date of Patent: Nov. 27, 2018

(54) PROTECTIVE FACE SHIELD ASSEMBLY

(71) Applicant: PAULSON MANUFACTURING CORPORATION, Temecula, CA (US)

(72) Inventor: Roy Paulson, Murietta, CA (US)

(73) Assignee: PAULSON MANUFACTURING CORPORATION, Temecula, CA (US)

( * ) Notice: Subject to any disclaimer, the term of this patent is extended or adjusted under 35 U.S.C. 154(b) by 0 days.

(21) Appl. No.: 15/908,541

(22) Filed: Feb. 28, 2018

(51) Int. Cl.
*A61F 9/06* (2006.01)
*A42B 3/22* (2006.01)
*A42B 3/24* (2006.01)

(52) U.S. Cl.
CPC .............. *A42B 3/225* (2013.01); *A42B 3/223* (2013.01); *A42B 3/24* (2013.01); *A61F 9/06* (2013.01)

(58) Field of Classification Search
CPC . A42B 3/222; A42B 3/20; A61F 9/028; A61F 9/06
See application file for complete search history.

(56) References Cited

U.S. PATENT DOCUMENTS

| | | | | |
|---|---|---|---|---|
| 2,406,092 A | * | 8/1946 | Meyer | A61F 9/06 2/8.1 |
| 3,026,525 A | * | 3/1962 | Gyorfy | A42B 3/225 2/202 |
| 4,021,858 A | * | 5/1977 | Neeld | A42B 3/08 2/9 |
| 4,853,973 A | * | 8/1989 | Boochard | A61F 9/06 2/434 |
| 5,483,699 A | * | 1/1996 | Pernicka | A42B 3/22 2/424 |
| 2016/0183623 A1 | * | 6/2016 | Didier | A42B 3/225 2/421 |

* cited by examiner

Primary Examiner — Tejash Patel
(74) Attorney, Agent, or Firm — The Maxham Firm

(57) ABSTRACT

A face shield assembly for use with a hard hat to protect a user from injury caused by an arc-flash event. Ventilation slots are provided at the sides of the assembly below an apparatus used for connecting the face shield assembly to a hard hat. Alternatively, lower front ventilation slots are provided, which also improve voice communication by the user. The face shield assembly can have either side or front ventilation slots, or both.

25 Claims, 13 Drawing Sheets

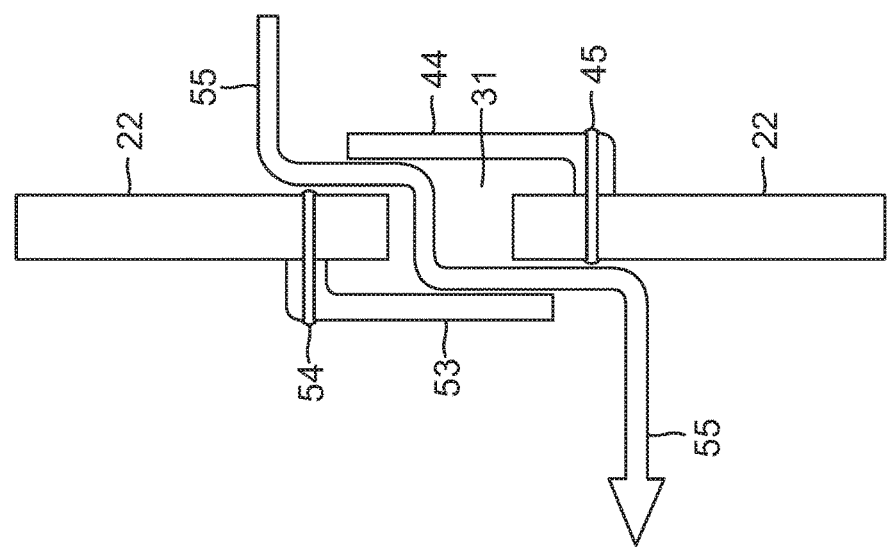

PROTECTIVE FACE SHIELD ASSEMBLY

FIELD OF INVENTION

The present apparatus relates generally to the field of safety devices which protect people from injury arising from electric-arc discharges and more particularly to protective face shields for use with safety helmets.

BACKGROUND OF THE INVENTION

Electrical-arc-flash hazards are a known threat in some workplaces and must be addressed to protect people who may be exposed to such dangerous conditions. Electric-arcs or flashes can result from short circuits developing from poor electrical grounding, failure of insulation, or workers inadvertently contacting exposed electrical circuit elements with objects such as tools. Electric-arcs have extremely high temperatures and near explosive power, and the energy they radiate can result in serious or fatal injury. To protect workers from exposure to such arc-flash events, a number of protective safety devices have been developed. In particular, face shields employing generally transparent windows comprised of compositions which have the ability for the user of the shield to see the workspace and, at the same time, have the ability to substantially block harmful radiation, are available. These devices are designed to provide protection against the thermal, optical, and mechanical hazards generated by arc-flash events. The protective compositions are referred to as energy absorbing materials and are classified by their calorie ratings, that is, the level of energy they have been tested or certified for.

The protective window of such a protective face shield is securely attached to the retainer structure of the shield and is structured to provide maximum protection to the user. In particular, the installation is designed to prevent radiation leaks around the periphery of the window.

Because of the need to protect a user from the electromagnetic energy of an arc-flash event, protective face shields have, of necessity, been relatively well sealed around the face of the user. Lack of adequate ventilation is a typical consequence of the face shield being sealed, and additions such as fans have been employed in some face shields to provide needed ventilation. Even then, moisture and fogging sometimes result because of inadequate provision for air to easily exhaust from near the front inside of the face shield. It has been difficult to ventilate arc shields because of the potential arc-flash energy that could enter the shield through vents or slots. Additionally, voice communication by the user is difficult and words or other sounds tend to be muffled from inside the face shield or maybe partially blocked from adjacent team members.

Generally related prior art devices are shown in FIGS. 1-3. These are provided for reference purposes, to show examples of protective face shields.

SUMMARY OF THE EMBODIMENTS OF THE INVENTION

A purpose of the present concept is to maintain electromagnetic energy and infrared energy protection while providing ventilation and enabling effective voice communication by the user.

Side slots in the inner frame of the face shield assembly, which are in offset registration with side slots in the shield frame, provide ventilation without degrading electromagnetic energy protection. The side slots also improve audible reception by the user since those slots arc located in the general area of the user's ears.

Additionally, lower front (generally in the user's chin area) slots may optionally be provided in the inner frame which are in offset registration with lower front slots in the shield frame. This combination of sower front slots provide enhanced ventilation and improve voice communication by the user, without degrading protection from dangerous energy events. The lower front slots would be configured to provide enhanced ventilation for the user in that outside air would enter the front slots and, by convection, exhaust from the side slots.

FIGS. 1-3 shows currently manufactured face shields that attach to hard hat safety helmets, and at least one of these is attached by mounting to the accessory slots of such helmets. For example, FIG. 3 includes a transparent window comprised of a composition which absorbs a specified fraction of the harmful radiation produced by an electric-arc, while offering a wide viewing angle.

BRIEF DESCRIPTION OF THE DRAWING

The purposes, features, and advantages of the disclosed structure will be more readily perceived from the following detailed description, when read in conjunction with the accompanying drawing, wherein;

FIGS. 11A-11E are exemplary partial, sectional schematic representations of structures creating semi-tortuous air flow paths, which structures can be employed with the upper side or the lower front, or both, vents of the embodiment of FIGS. 4-10.

DETAILED DESCRIPTION OF THE PREFERRED EMBODIMENTS

Figure 1:
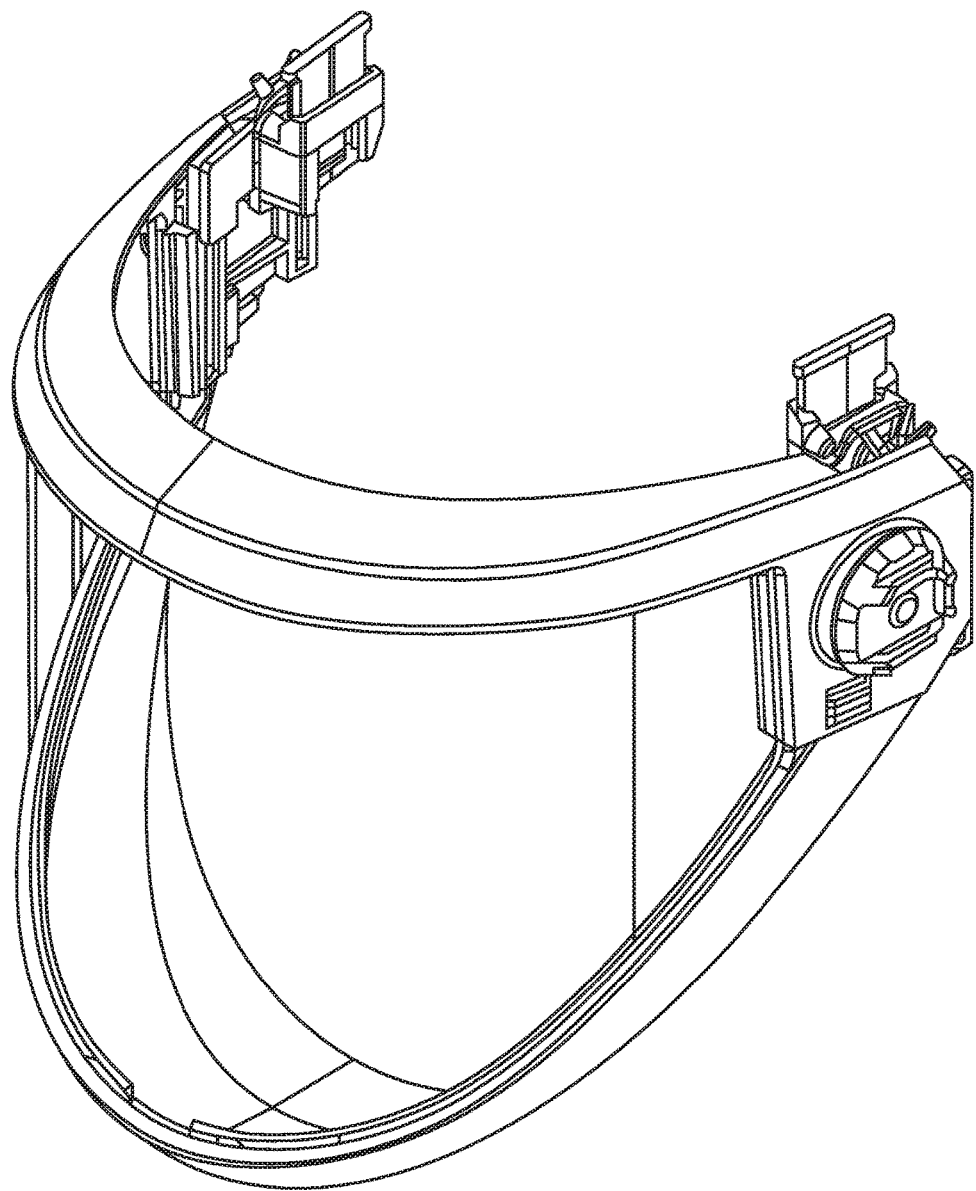
FIGS. 1-3 show currently available electric-arc face shields.
Figure 2:
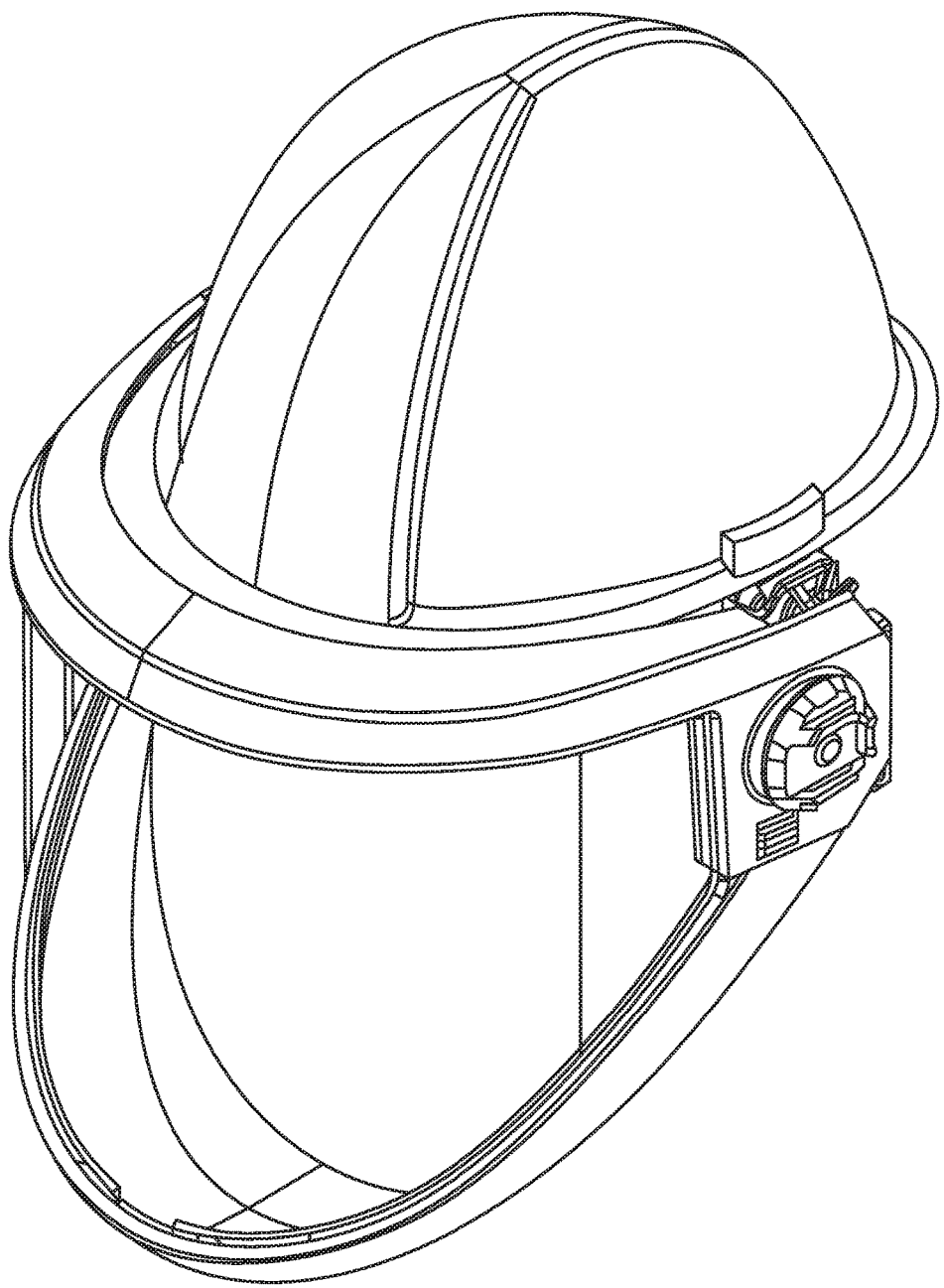
Figure 3:
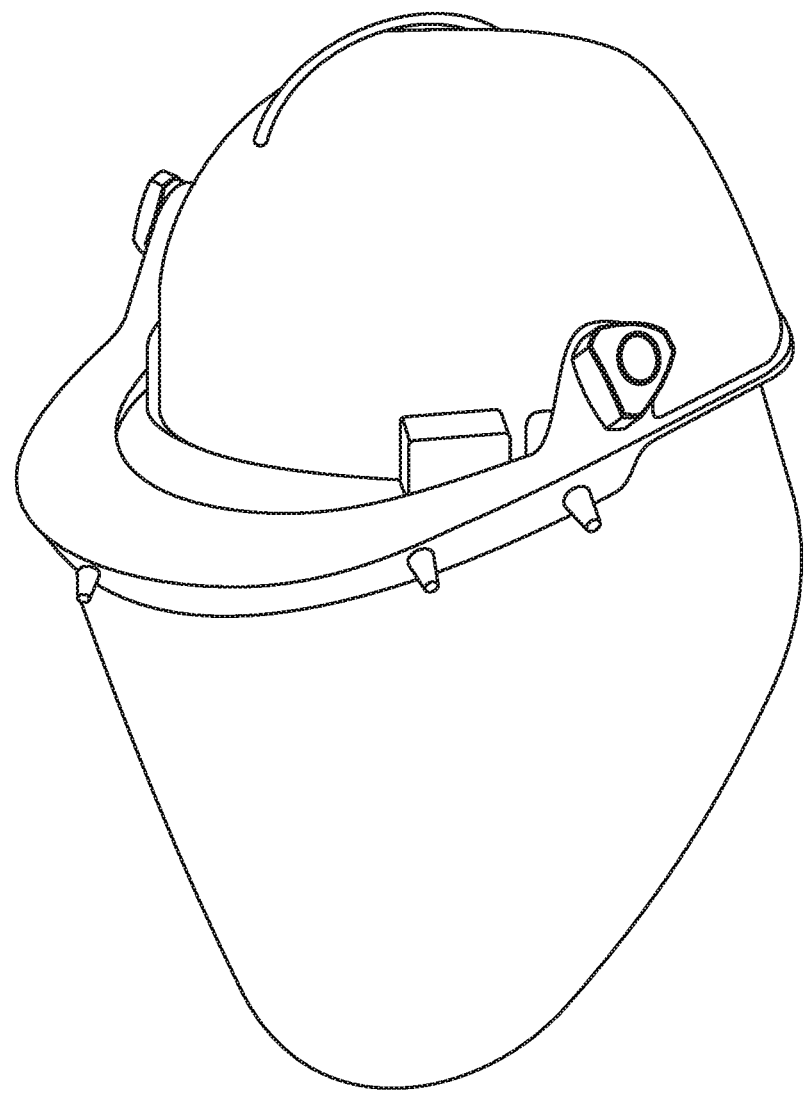
Figure 4:
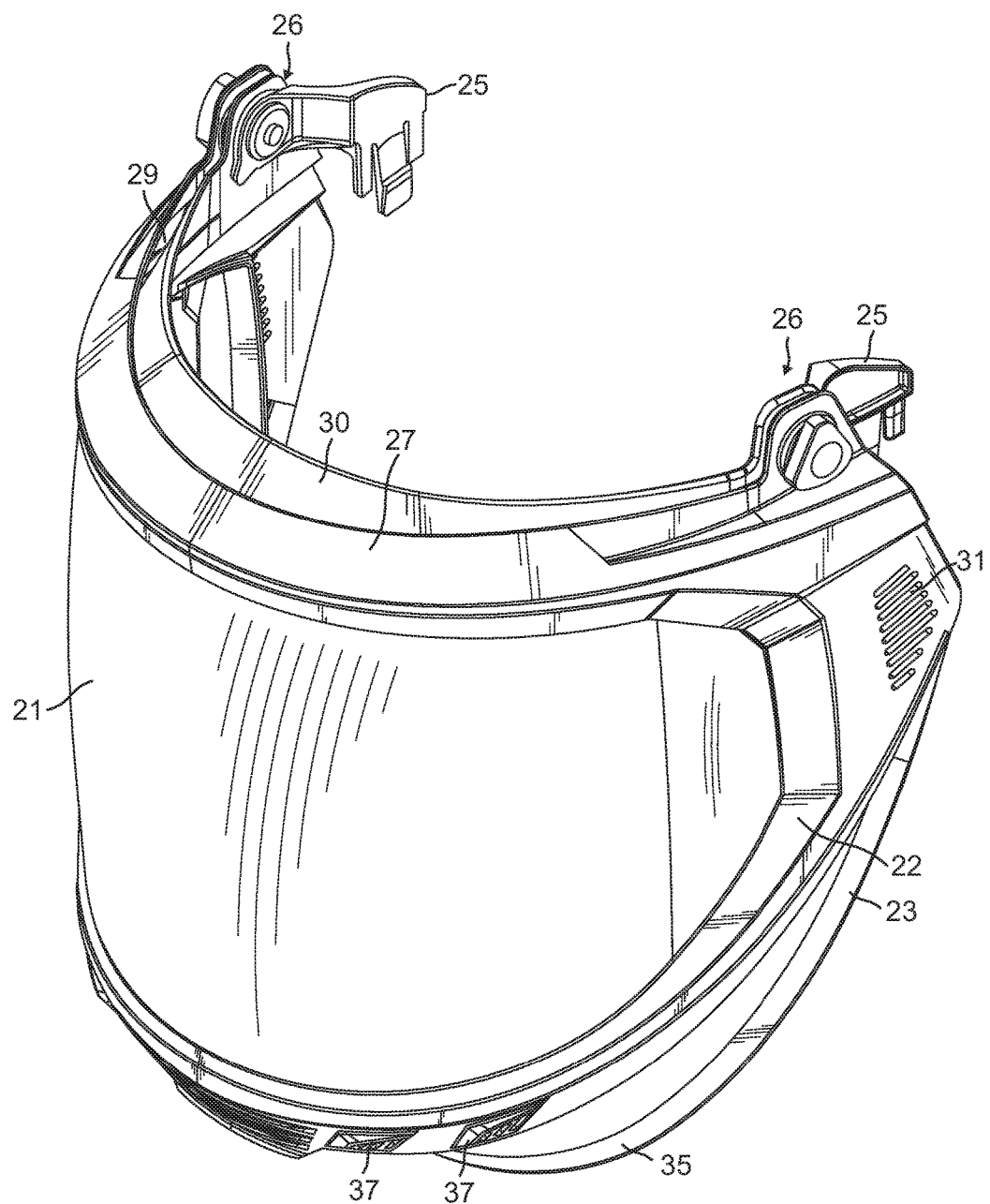
FIG. 4 is a perspective view of an embodiment of the protective face shield assembly of this invention.
Figure 5:
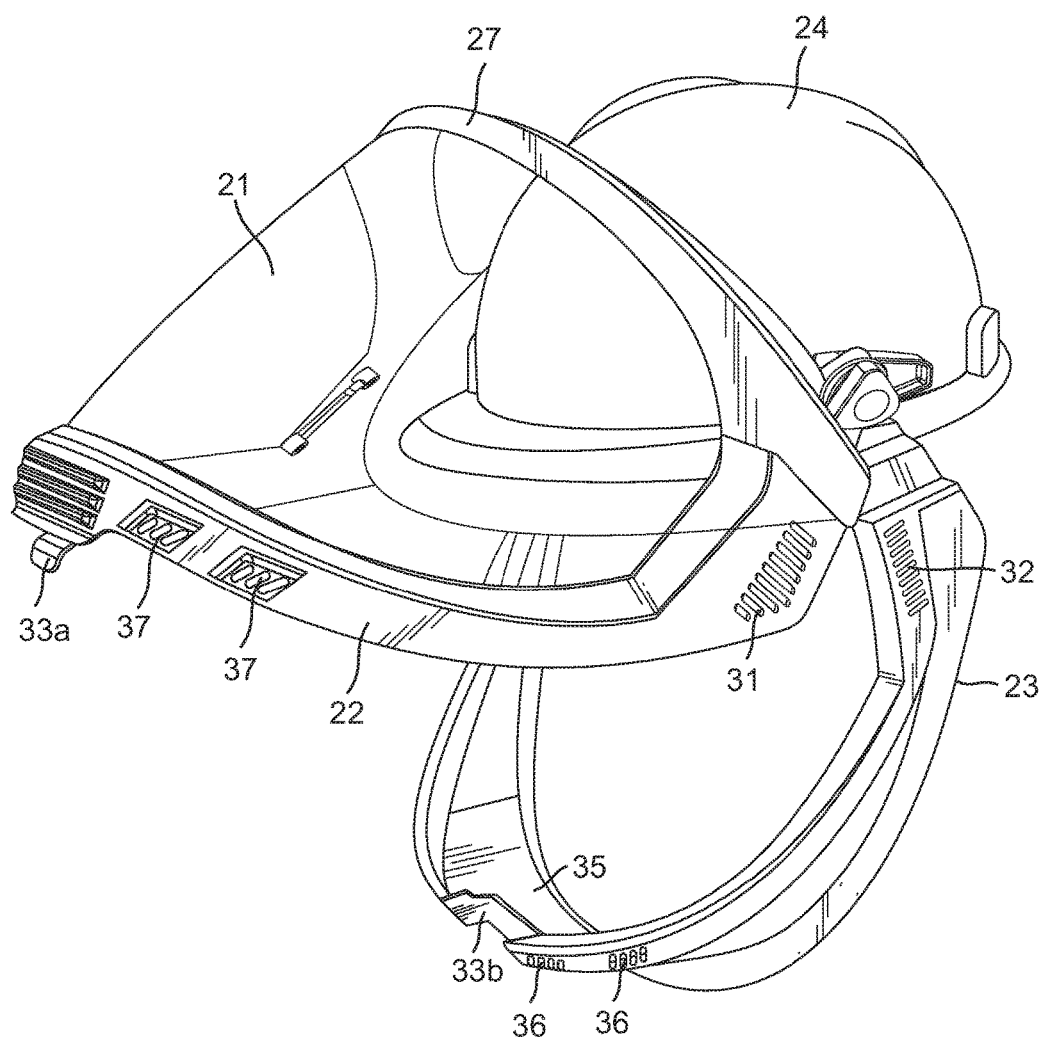
FIG. 5 is a perspective view of die face shield assembly of FIG. 4 with the face shield in the raised or stowed position.
Figure 6:
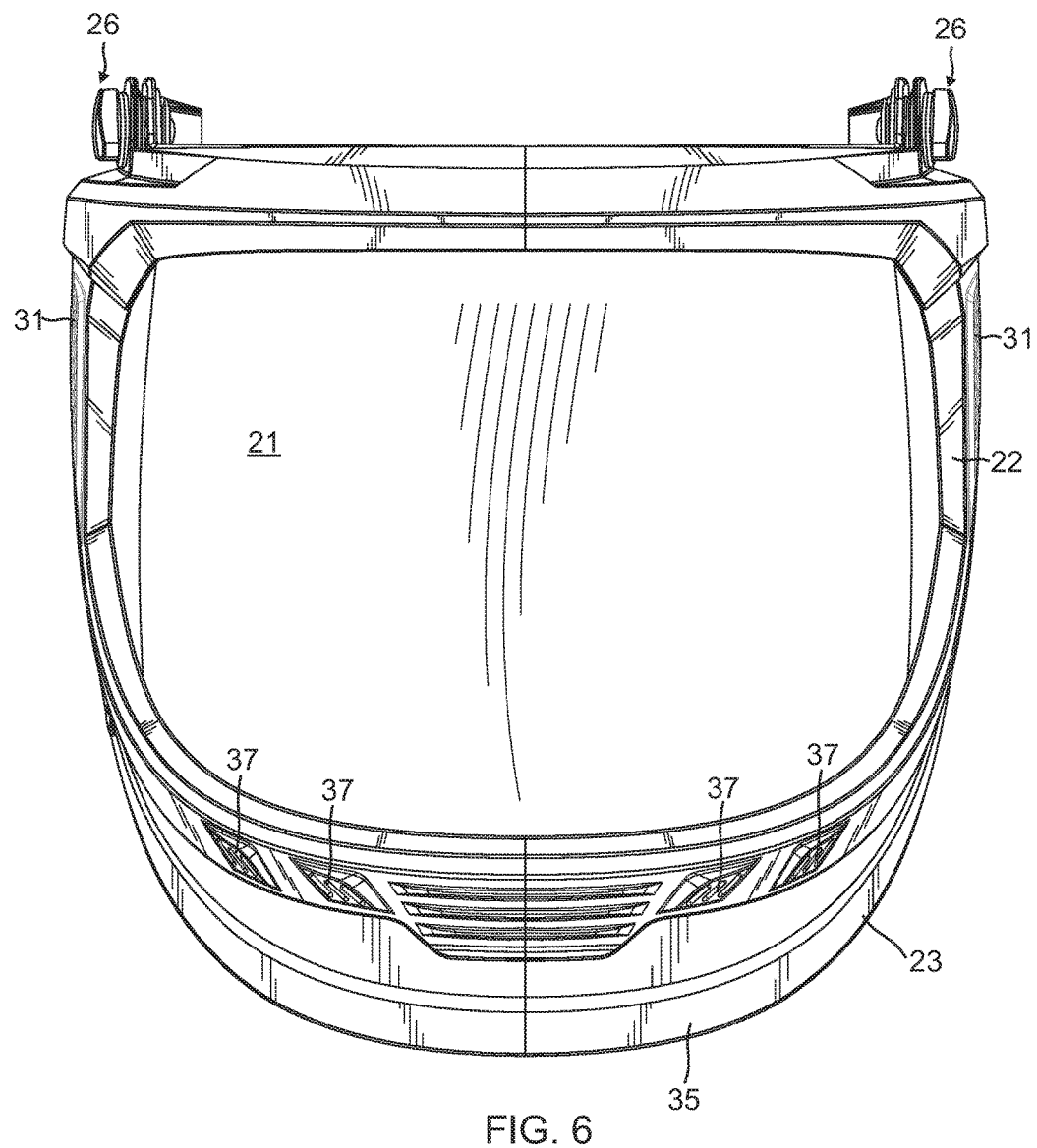
FIG. 6 is a front view of the face shield assembly of FIG. 4.
Figure 10:
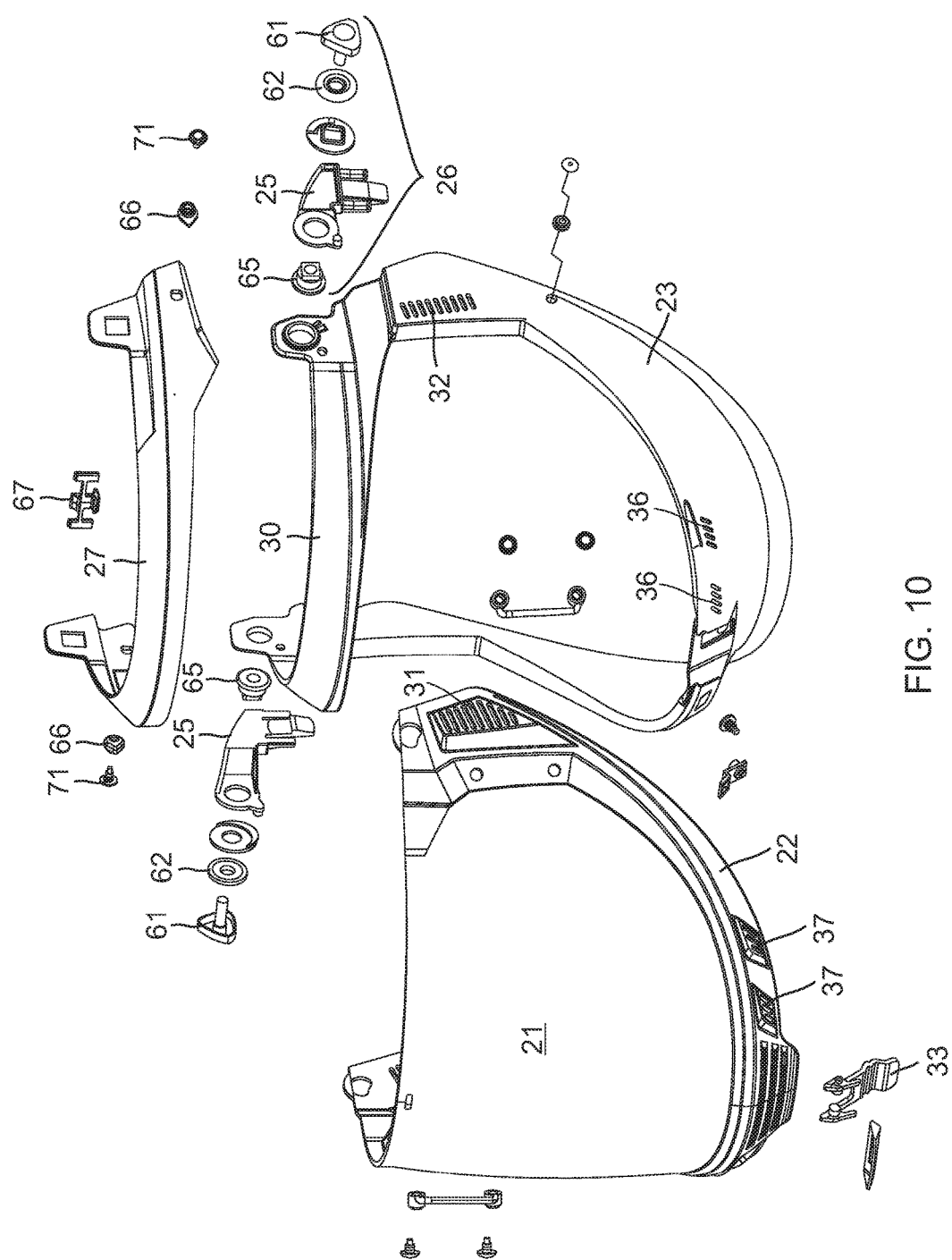
FIG. 10 is a perspective exploded view of the subject face shield assembly of FIG. 4.

With reference now to the drawing, and more particularly to FIGS. 4-6 thereof, face protective window 21 is mounted to shield frame 22 which is, in turn, pivotably mounted to inner frame 23. The inner frame may be mounted to, or be removably mountable to, hard hat 24 with helmet adapter 25. The helmet adaptor and the inner frame are rotatably or pivotably coupled together by means of coupling mechanism 26, the components of which are shown in FIG. 10. Their functions are immediately apparent and need not be specifically described here. Pivotable coupling mechanism 26 typically has a detent mechanism included, as is described later herein.

Below (when in use) the pivot mechanism are a plurality of through side slots 31 in shield frame 22. These side slots are generally located in front of the user's ears, somewhat adjacent to their temples and above their cheekbones. In offset registration with side slots 31 are a generally similar plurality of through side slots 32 (FIG. 5) in inner frame 23. This offset registration is more clearly depicted in FIG. 8. Latch mechanism 33a, 33b provides positive engagement of the shield frame with the inner frame when in the deployed position, while at the same time, enabling those frames to be quickly and easily disengaged so that the face shield can be pivoted to the stowed position (FIG. 5).

As shown, the lower, front (chin area) portion 35 of inner frame 23 is formed with a plurality of front slots 36, shown in groups of four. Shield frame 22 is formed with a plurality of front slots 37, shown here in groups of three, which are in offset registration with inner frame front slots 36 when the shield frame is in the deployed position, as shown in FIG. 4. In the manner of slots 31 and 32, slots 36 and 37 are configured in groups as shown. The actual number of slots in each group is not fixed or limited, and related offset slots need not have the same number in each of the matching groups. These front slots are an option and need not be combined with side slots 31, 32.

Figure 8:
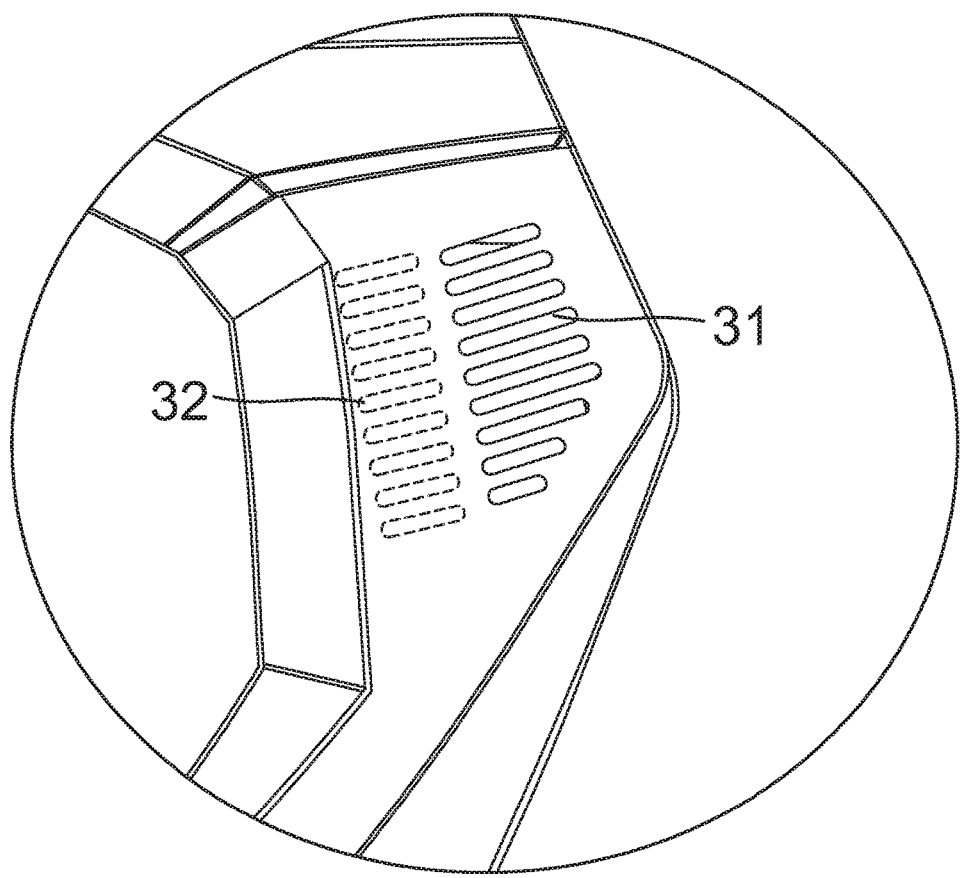
FIG. 8 is an enlarged, partially broken away side view of the side vents of the face shield assembly.

As shown in FIG. 8, inner frame slots 32 are generally aligned with shield frame slots 31, except that they are offset with respect to each other. In other words, there is essentially no direct opening from outside the shield frame to and through the slots of the inner frame. When the face shield is in the deployed position (see FIG. 4) the inner surface of the side of the shield frame in that portion in which are slots 31 is slightly spaced from outer surface of inner frame 23 to permit air flow between those facing portions of the inner and shield frames. Thus, ventilation air flow is outwardly through inner frame slots 32, then laterally a short distance and then out through shield frame slots 31 in a semi-tortuous manner (see FIG. 11).

This arrangement effectively protects the user from arc-flash injury in that there is no direct passageway from outside the face shield assembly to the inside, while the indirect air flow provides ventilation for the user's face.

With reference now to FIGS. 5 and 9, lower front slots 36 and 37 are shown in full functioning detail.

Figure 9A:
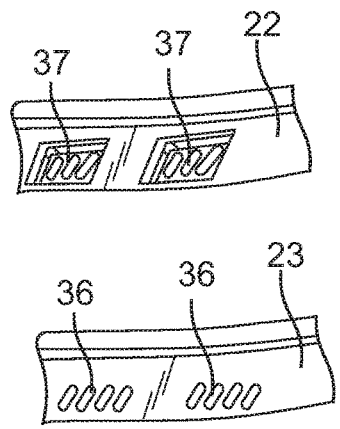
FIG. 9A is an enlarged, partially broken away bottom front view of the lower front vents of the face shield assembly of FIG. 4 with the face shield in a partially open position.
Figure 9B:
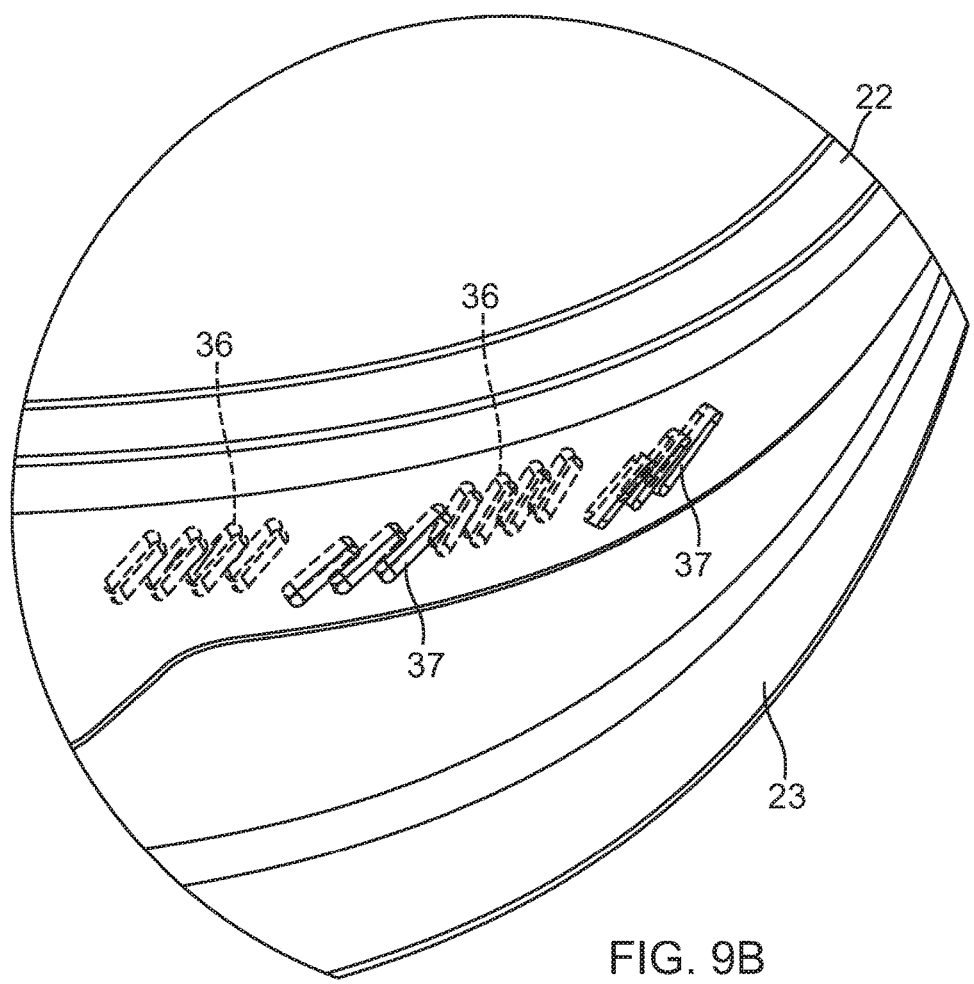
FIG. 9B is an enlarged, partially broken away bottom front view of the lower front vents of the face shield assembly of FIG. 4 with the face shield in a deployed position.

A portion of the face shield is shown in partially raised position in FIG. 9A. When the face shield is in deployed position (FIG. 9B), the slot groups are in offset registration so that slots 37 in shield frame 22 do not overlap slots 36 in inner frame 23. As shown in FIG. 9B, slots 36 are behind the lower front portion of shield frame 22 and aligned so that there is no direct path from any one slot 36 out through any slot 37. Further, the overlapping portions of lower front inner and shield frames 23 and 22, respectively, are spaced only sufficiently to permit air to flow between them and through slots 37, then laterally between the inner and shield frames, and then inwardly through slots 36. Examples of structures to create such semi-tortuous air flow paths are shown in FIG. 11.

The face shield assembly is configured so that cooler outside air would normally flow inwardly through slots 37, then through slots 36, and upwardly and outwardly through slots 32, then laterally between the side petitions of the inner and shield frames, and finally exhausting out through slots 31 in the shield frame. However, under different conditions the air could flow in reverse directions, and still provide effective ventilation.

It should be noted that the face shield assembly provides improved ventilation with only side slots 31, 32, or only with front slots 36, 37, and the combination of front and side slots is an alternative that provides a higher level of ventilation for the user.

Another benefit of front slots 36, 37, as is true of side slots 31, 32, is the provision of enhanced communication. Without the front slots, the user's voice could be somewhat muffled and possibly hard to hear by a nearby person. These front slots significantly improve the ability of the user to communicate with others nearby. The ability of the user to clearly verbally communicate with a nearby team member can be critical in situations where arc-flash events are possible. Likewise, the user of the protective face shield has greater ability to clearly hear sounds, including voices of nearby team members, due to the location generally near the user's ears of slots 31, 32.

As shown in the drawing, the number of slots 31 equals the number of slots 32, while more slots 36 than mating offset slots 37 are presented. The actual number of slots in any group of slots 31, 32, and 36, 37 can vary and mating groupings may have equal or unequal numbers of slots. As shown, the mating slot groups are offset and closely spaced so air passes through them along a slightly tortuous path and there is no direct, unimpeded route from inside to outside the shield assembly. This provides ventilation and enhanced communication while, at the same time, protecting the user from arc-flash injury.

FIG. 10 is provided to show the elements of the protective face shield of FIG. 4 and the structure of how it is connectable to a hard hat. The rotatable coupling mechanism 26 is, at least in part, coupled with hard hat adapter 25.

While this exploded view is not necessary for a full understanding of the protective face shield assembly already described, it is presented for further detail of some of the elements of the complete assembly.

Pivot screw 61 provides the tensioning and resulting function of the pivots on each side of the shield. As stated earlier, the shield pivots and inner frame 23 remain in the deployed position whenever the assembly is mounted to a hard hat.

Function washer 62 includes an O-ring set into a groove to provide consistent, or even, friction associated with the pivot screw. Detent washer 63 is part of the mechanism that allows one or more angles of the stowed position of the shield frame.

Helmet adapter 25 is configured to snap into the slots on either side of a conventional hard hat to enable the entire assembly to be mounted onto a hard hat.

Pivot nut 65 fits through helmet adapter 25 and locates all of the pivot components and inner frame 23 to shield frame 22. Pivot screw 61 screws into the pivot nut.

Amp retainer 66 is mounted to the inside of cap bracket 27. This retains the ends of shield frame 22 and includes locking mechanism 67 which secures shield 21 in the assembly. Rivet 71 fixedly attaches the amp retainer to the cap bracket.

Catch 72 is mounted on inner frame 23 and engages with latch lever 33 to hold the shield in deployed (closed) position.

Flange seal cover 73 is configured to block an arc-flash from entering the interior of the assembly in the area of the latching mechanism.

As shown in FIGS. 4, 5, and 10, the front shield is comprised of generally, or semi, transparent window or lens 21 which is mounted to, or molded together with, shield frame 22. That unitary structure is, preferably, detachably coupled to cap bracket 27. It is the cap bracket that is rotatably coupled with inner frame 23 by means of mechanism 26. Mechanism 26 preferably includes a detenting mechanism to lightly but positively hold the shield frame in the stowed position, while enabling the shield frame to return to the deployed position (FIG. 4) with a slight hand nudge or even with a nod of the user's head. The detenting mechanism may also have intermediate positions of minor or temporary stability between the stowed and the deployed positions.

The structure described provides indirect, or semi-tortuous, ventilation paths through slot group pairs 31, 32, or 36, 37, or both, while protecting against infrared and electromagnetic energy injury. The window 21, the shield frame 22, and the inner frame 23 are all made of the same energy absorbing material having the same calorie rating for arc-flash protection of the user.

Any electromagnetic energy that passes through the shield frame vents or slots is absorbed by the inner frame at the mating vent location. Thus the vent pairs accept air transfer and block electromagnetic energy. At the same time, the ventilation slots provide improved sound and verbal communication from and to the user of the protective face shield.

In configurations without side slots 31, 32, the lower front slots 36, 37, can provide adequate ventilation from inside the protective face shield assembly in combination with space or gap 29 at the top between the inner frame and the shield frame, as shown in FIG. 4. The top front 30 of inner frame 23 is formed so that when the shield is in the deployed position, a gap remains between cap bracket 27 and top front 30 of the inner frame. However, that gap slopes upwardly and rearwardly so no dangerous energy can get through to the inside of the face shield assembly.

Examples of possible structures that can be employed to provide the described semi-tortuous air flow paths are shown in FIG. 11.

Figure 11B:
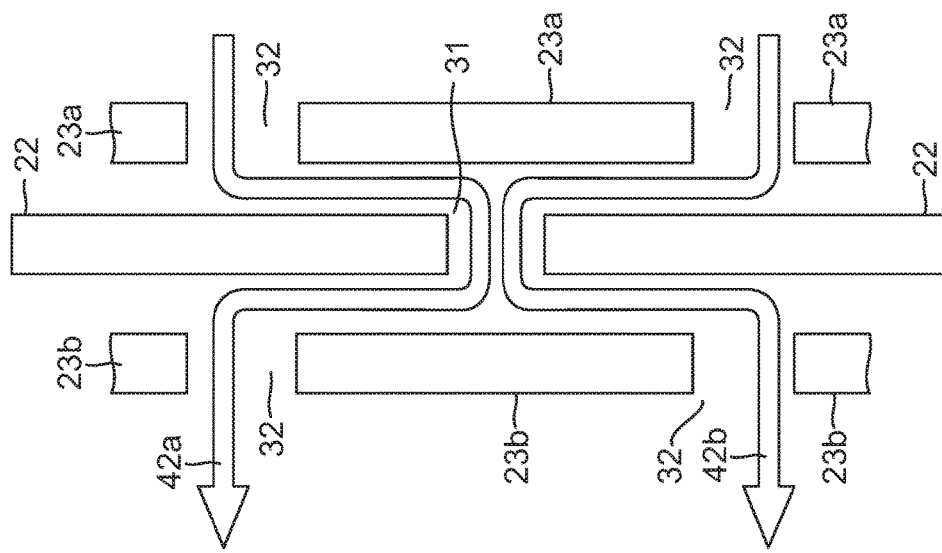
Figure 11A:
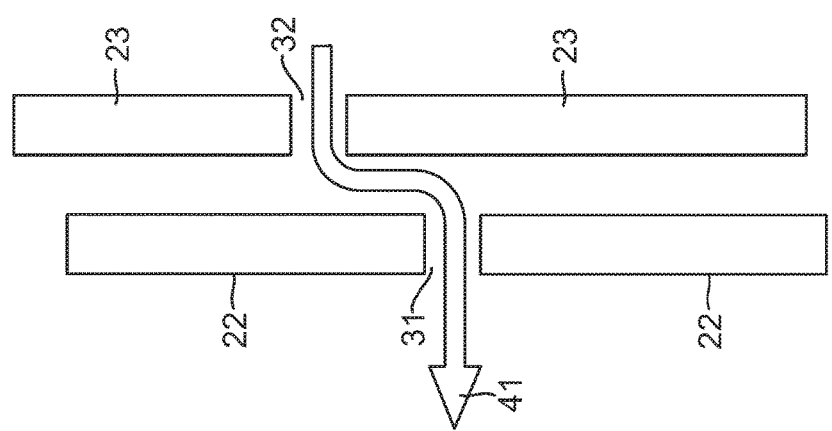

A rather straightforward indirect air flow path is shown in FIG. 11A. This represents the type of structures contemplated in the FIG. 4 embodiment. For simplicity, air flow is represented by arrow 41 as it passes through slot 32 in inner frame 23 and indirectly through a slot 31 in shield frame 22. The elements could be reversed, as could the air flow.

Figure 7:
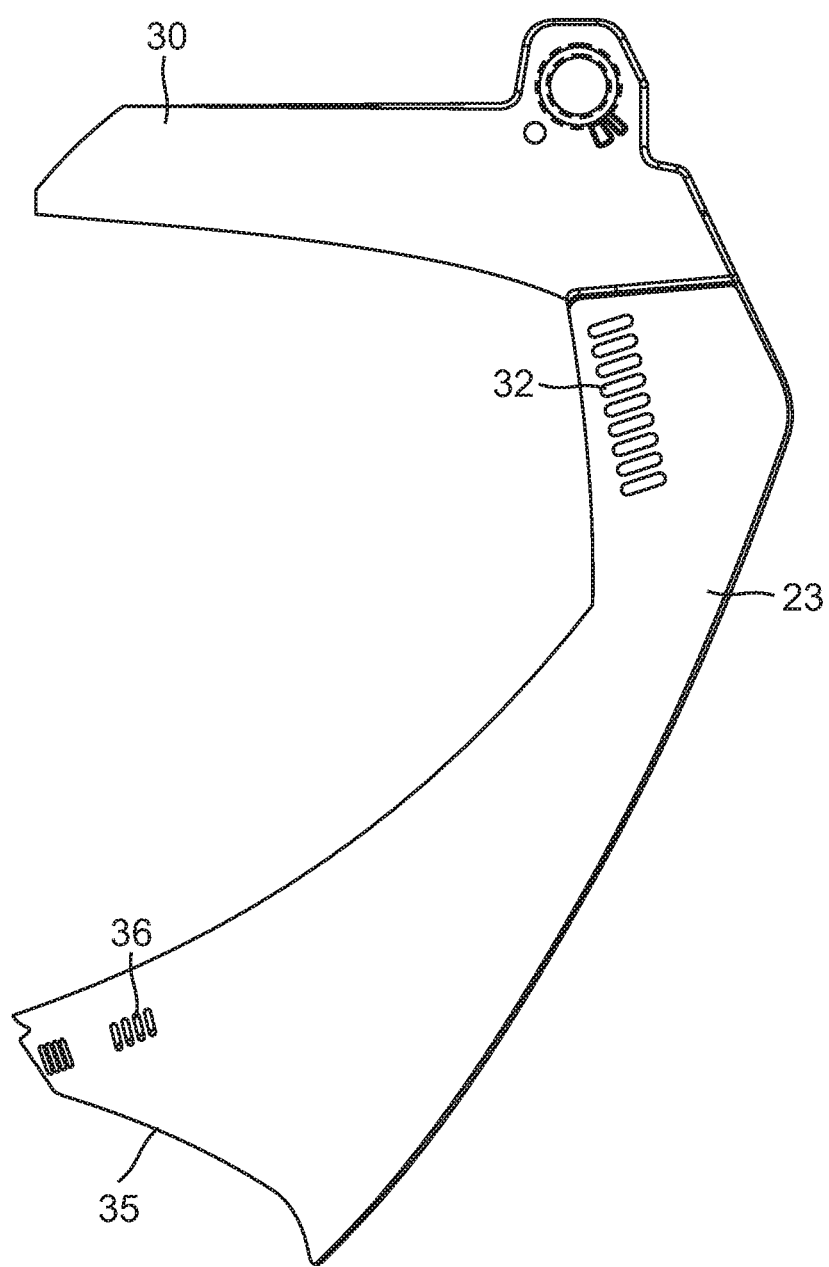
FIG. 7 is a side view of the inner frame of the face shield assembly of FIG. 4.

An alternative structure is shown in FIG. 11B. This is what the indirect flow might be if either inner frame 23 or shield frame 22 is formed with an overlap portion to create a type of sandwich structure. For example, the portion of shield frame 22 with slots 31 slides between elements 23a and 23b of inner frame 23. In this alternative, slots 32 maybe similar to those previously shown (FIGS. 5, 7, and 8) or larger and they create a double indirect flow. As with FIG. 11A, the elements could be reversed so that there are inside and outside segments on shield frame 22 and the slot area 32 of inner frame 23 would be the internal element, creating the indirect flow paths.

Figure 11D:
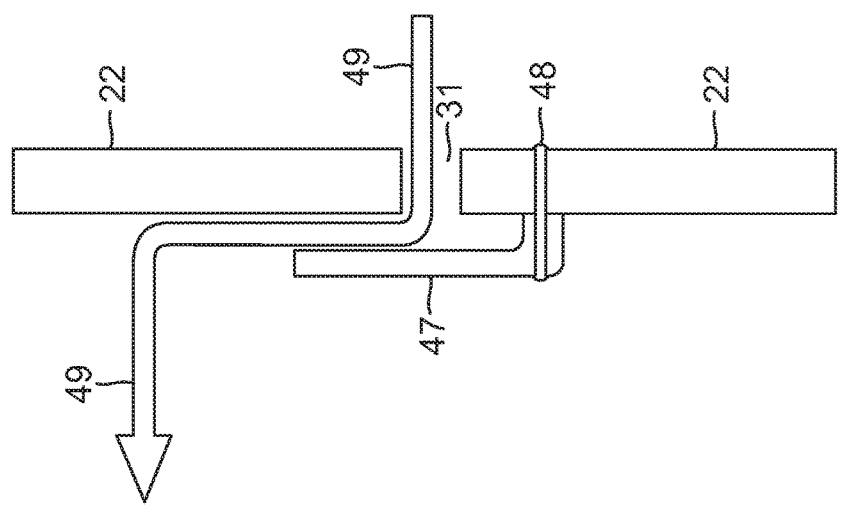
Figure 11C:
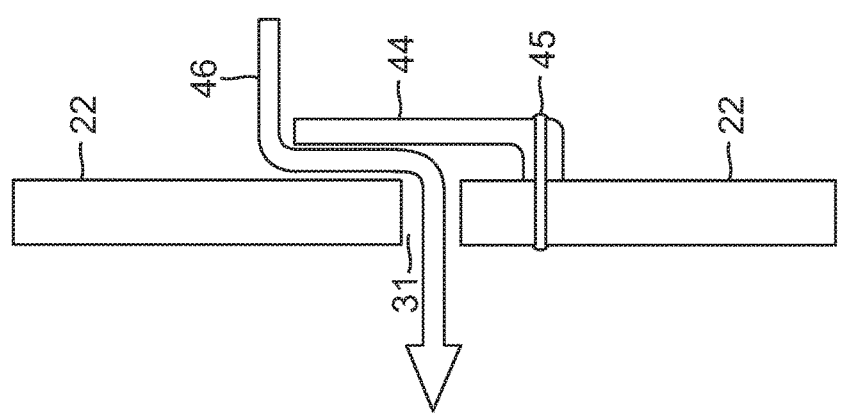

A second alternative tortuous air flow path is shown in FIG. 11C. In this embodiment a separate air deflector 44 is secured to shield frame 22 by means of fastener 45 to create tortuous air flow path 46. This concept can be employed in relation to any vent slots or slot groups that can be formed in this face shield assembly.

FIG. 11D is much like the air flow path structure of FIG. 11C. Here air deflector 47, secured to shield frame 22 by fastener 48, results in air flow path 49.

Another air flow structure is shown in FIG. 11B, which modifies the embodiment of FIG. 11C. This adds a second air deflector 53 secured to shield frame 22 by means of fastener 54 to result in air flow path 55.

It can be understood that other alternative structures by which tortuous air flow paths are created can be realized, which enables air flow into or out of the face shield interior while protecting the user from an arc-flash event. The access between inside and outside is indirect air flow and the structure prevents direct arc-flash access to the user's face or head.

Not only does the structure described herein protect the user against electromagnetic radiation, including infrared energy, it also protects against plasma and connected heat, against impact, and against molten metal splash. These protection ratings generally range from 12 to 40 calories, and can have a rating as high as 100 calories.

What is claimed is:

1. A protective face shield assembly for use with a safety helmet, the face shield assembly comprising:
    an inner frame configured to be detachably mounted to the safety helmet, said inner frame having a plurality of through side slots in a position spaced from the detachable mounting;
    a shield frame rotatably mounted to said inner frame and having a stowed position and a deployed position, said shield frame having a side portion with a plurality of through side slots, said shield frame side portion overlapping said inner frame side portion when said shield frame is in the deployed position in a manner that said shield frame side slots are in offset registration with said inner frame side slots so that the respective side slots have substantially no direct overlap to thereby provide indirect ventilation and provide protection from energy from an arc-flash event; and
    a face protective window mounted to said shield frame, said window being raised together with said shield frame when in the stowed position.

2. The protective face shield assembly of claim 1, wherein said overlapping side portions are in non-contacting spaced relationship.

3. The protective face shield assembly of claim 1, wherein said overlapping side portions are in close, non-contacting spaced relationship, the space between said overlapping side portions being sufficient to permit air flow in that space.

4. the protective face shield assembly of claim 1, wherein said window is comprised of semi-transparent material.

5. The protective face shield assembly of claim 1, wherein said window is transparent.

6. The protective face shield assembly of claim 1, and further comprising:
    said inner frame having a lower front portion with a plurality of through front slots;
    said shield frame having a lower front portion with a plurality of through front slots:
    said shield frame lower front portion overlapping said inner frame lower front portion with said respective front slots being in offset registration when said shield frame is in the deployed position so that said respective front slots have substantially no direct overlap to thereby provide indirect ventilation, enable audio transmission, and provide protection from energy from an arc-flash event.

7. The protective face shield assembly of claim 6, wherein said overlapping lower front portions are in non-contacting spaced relationship.

8. The protective face shield assembly of claim 6, wherein said overlapping lower front portions are in close, non-contacting spaced relationship, the space between said overlapping lower front portions being sufficient to permit air flow in that space.

9. A protective face shield assembly for use with a safety helmet, the face shield assembly comprising:
   an inner frame configured to be detachably mounted to the safety helmet, said inner frame having a plurality of through front slots in a lower front portion;
   a shield frame rotatably mounted to said inner frame and having a slowed position and a deployed position, said shield frame having a lower front portion with a plurality of through front slots, said shield frame lower front portion overlapping said inner frame side portion when said shield frame is in the deployed position in a manner that said shield frame lower front slots are in offset registration with said inner frame lower front slots so that the respective lower front slots have substantially no direct overlap to thereby provide indirect ventilation and provide protection from energy from an arc-flash event; and
   a face protective window mounted to said shield frame, said window being raised together with said shield frame when in the stowed position.

10. The protective face shield assembly of claim 9, wherein said overlapping lower front portions are in non-contacting spaced relationship.

11. The protective face shield assembly of claim 9, wherein said overlapping lower front portions are in close, non-contacting spaced relationship, the space between said overlapping lower front portions being sufficient to permit air flow in that space.

12. The protective face shield assembly of claim 9, wherein said window is comprised of semi-transparent material.

13. The protective face shield assembly of claim 9, wherein said window is transparent.

14. The protective face shield assembly of claim 9, and further comprising a gap between a top portion of said inner frame and a top portion of said shield frame.

15. A protective face shield assembly for use with a safety helmet, the face shield assembly comprising:
   an inner frame configured to be detachably mounted to the safety helmet, said inner frame having a side portion in a position spaced from the detachable mounting;
   a shield frame rotatably mounted to said inner frame and having a stowed position and a deployed position, said shield frame having a side portion overlapping said inner frame side portion when said shield frame is in the deployed position;
   at least one of said inner frame side portion and said shield frame side portion being configured with through side vent openings;
   a baffle structure mounted to at least one of said inner frame and said shield frame, said baffle structure being spaced from and substantially covering said side vent openings in said at least one of said inner frame side portion and said shield frame side portion to provide indirect ventilation flow between the inside of the face shield assembly and the outside thereof and to provide protection from energy from an arc-flash event; and
   a face protective window mounted to said shield frame, said window being raised together with said shield frame when in the stowed position.

16. The protective face shield assembly of claim 15, wherein said baffle structure provides a semi-tortuous path for air flow between the inside and the outside of the face shield assembly.

17. The protective face shield assembly of claim 15, wherein said overlapping side portions are in close, non-contacting spaced relationship, the space between said overlapping side portions being sufficient to permit air flow in that space.

18. The protective face shield assembly of claim 15, wherein said window is comprised of semi-transparent material.

19. The protective face shield assembly of claim 15, and further comprising;
   said inner frame having a lower front portion;
   said shield frame having a lower front portion:
   at least one of said inner frame lower front portion and said shield frame lower front portion being configured with through from slots; and
   a baffle structure mounted to at least one of said inner frame and said shield frame, said baffle structure being spaced from and substantially covering said through front slots in said at least one of said inner frame lower front portion and said shield frame lower front portion to provide indirect ventilation flow between the inside of the face shield assembly and the outside thereof and to provide protection from energy from an arc-flash event.

20. The protective face shield assembly of claim 19, wherein said overlapping lower front portions are in non-contacting spaced relationship.

21. The protective face shield assembly of claim 19, wherein said overlapping lower front portions are in close, non-contacting spaced relationship, the space between said overlapping lower front portions being sufficient to permit air flow in that space.

22. A protective face shield assembly for use with a safety helmet, the face shield assembly comprising:
   an inner frame configured to be detachably mounted to the safety helmet, said inner frame having a lower front portion;
   a shield frame rotatably mounted to said inner frame and having a stowed position and a deployed position, said shield frame having a lower front portion overlapping said inner frame lower front portion when said shield frame is in the deployed position;
   at least one of said inner frame lower front portion and said shield frame lower front portion being configured with through front slots;
   a baffle structure mounted to at least one of said inner frame and said shield frame, said baffle structure being spaced from and substantially covering said front vent openings in said at least one of said inner frame lower front portion and said shield frame lower front portion to provide indirect ventilation flow between the inside of the face shield assembly and the outside thereof and provide protection from energy from an arc-flash event; and
   a face protective window mounted to said shield frame, said window being raised together with said shield frame when in the stowed position.

23. The protective face shield assembly of claim 22, wherein said overlapping lower front portions are in non-contacting spaced relationship.

24. The protective face shield assembly of claim 22, wherein said overlapping lower front portions are in close, non-contacting spaced relationship, the space between said overlapping lower front portions being sufficient to permit air How in that space.

25. The protective face shield assembly of claim 22, wherein said window is comprised of semi-transparent material.

\* \* \* \* \*